United States Patent [19]

Ozkan

[11] 4,450,231
[45] May 22, 1984

[54] IMMUNOASSAY FOR DETERMINATION OF IMMUNE COMPLEXES WITH POLYMER-COATED PLASTIC BASE

[75] Inventor: Adil N. Ozkan, Denver, Colo.

[73] Assignee: Biostar Medical Products, Inc., Boulder, Colo.

[21] Appl. No.: 363,967

[22] Filed: Mar. 31, 1982

[51] Int. Cl.³ ............................................. G01N 33/54
[52] U.S. Cl. ........................................ 435/7; 435/293; 436/506; 436/507; 436/529; 436/531; 436/538; 436/539; 436/809
[58] Field of Search ................... 435/7, 293; 436/506, 436/538, 539, 821, 507, 529, 531, 809

[56] References Cited

U.S. PATENT DOCUMENTS

| | | | |
|---|---|---|---|
| 4,143,124 | 3/1979 | Masson | 436/821 X |
| 4,146,640 | 3/1979 | Lenhard | 436/821 X |
| 4,153,417 | 5/1979 | Hallgren | 436/821 X |
| 4,162,895 | 7/1979 | Cambiaso | 436/821 X |
| 4,233,286 | 11/1980 | Soothill | 436/821 X |

OTHER PUBLICATIONS

"Manual of Clinical Immunology", N. R. Rose et al., eds., Chapt. 90, pp. 669–675, *American Society for Microbiology*, Washington, D.C., 1976.
Chemical Abstracts, 96: 179327u (1982).
Chemical Abstracts, 96: 120507z to 120514z (1982).

*Primary Examiner*—Sidney Marantz
*Attorney, Agent, or Firm*—Horace B. Van Valkenburgh; Jerry W. Berkstresser

[57] ABSTRACT

An immunoassay of a specimen of a serum or the like to determine immune complexes, includes producing on a plastic base a layer of a non-proteinaceous, non-ionic polymer which will adhere to the plastic base and has the capability of absorbing immune complexes of the specimen, placing a specimen on the layer and treating the layer to produce an indication of the amount of immune complexes. The polymer may be polyethylene glycol, dextran, polyvinyl chloride, a polymeric polyol or an adduct of polyethylene glycol. Washing with conventional solutions, addition of an antihuman IgG coupled with an enzyme and addition of a substrate reactive therewith, are similar to the ELISA test, with color measurement as by spectrophotometer. Or, the addition of anti IgG-$I^{125}$ and measurement by a scintillation counter may be used. The ethylene glycol may range in molecular weight from 2,000 to 20,000, although 6,000 to 8,000 is preferred. A product for use in such an assay is a plate having wells or a test tube formed of plastic, polystyrene and polyvinyl chloride being preferred, with a layer of such non-proteinaceous, non-ionic layer on the plate wells or the cavity of the test tube. This product, if it is not to be used immediately, should be provided with a layer or film protecting the polymer layer from the air.

16 Claims, 4 Drawing Figures

IMMUNOASSAY FOR DETERMINATION OF IMMUNE COMPLEXES WITH POLYMER-COATED PLASTIC BASE

This invention relates to a method of performing an immuno assay of a specimen of a serum or the like, as well as to an article for use in performing such an assay and a method for making such article.

BACKGROUND OF THE INVENTION

All of the previously developed immunoassays in common use rely on a coating of a protein on a solid phase base, in order to react with immune complexes in the specimen of serum, spinal fluid or the like. The presence of such immune complexes in such a specimen is indicative that a patient, from whom such a specimen was taken, has a condition such as rheumatoid arthritis, tumor, hepatitis, viral infection or the like. The ELISA test, described more particularly hereinafter, involves coating a solid phase base with a protein, washing with specified solutions, and placing the serum or other sample to be tested on the protein, to permit the protein to absorb the immune complexes in the specimen. An enzyme labeled anti-species globulin, such as anti-human IgG coupled with an enzyme such as a phosphatase, is added and permitted to stand for a desired period of time, followed by washing a number of times with a predetermined solution. Then a substrate is added, which will react with the material then attached to the protein and normally change color, dependent on the amount of immune complex which has been bound. With a p-nitro phenyl phosphate, the color produced is yellow, but with other substrates, the color may be different. After a period of time, such as 30 minutes or more, the color change may be observed visually for a generally qualitative determination, although through the use of a spectrophotometer, a more accurate reading may be obtained than could be obtained visually.

Other in vitro assays for the detection of immune complexes include the Raji cell radioimmuno assay which measures (or quantitates) the amount of immune complexes through the use of a radioactive material such as an anti-IgG-$I^{125}$ labeled antiserum. After washing off the excess rabiolabeled antiserum, the amount of immune complexes reactive with the radioactive material may be ascertained through use of a scintillation counter. The Raji cell radioimmunoassay test is described in *In Vitro Methods in Cell-Mediated and Tumor Immunity* Section D, chapter 52 (Academic Press 1976, edited by Bloom, B. and J. David).

Since each of the previous tests require protein for initial reaction with a specimen, it is apparent that a much less expensive material to form a layer on a solid phase base would reduce quite materially the cost of the material used in the immunoassay and thus reduce the ultimate cost. In addition, the use of radioactive material ordinarily requires a special permit, and, more particularly, numerous precautions in handling and use. In addition, the radio-active material is quite expensive and hazardous.

Among the objects of this invention are to provide a novel method of performing an immunoassay of a specimen of a serum or the like to determine immune complexes; to provide such a method which involves the use of a considerably less expensive material than the protein required for previous types of assays; to provide such a method which will produce reliable and reproducible results; to provide such a method which can be carried out with more ease and a more simple manner than in similar tests; to provide an article which is readily produced in quantity and which will reduce considerably the time involved in the actual assay; to provide such an article which can be made so that it can be stored for long periods of time; to provide a method of making such an article, by which the article can be made effectively and efficiently; and to provide such a method which can be carried out easily and effectively and at a significantly lower cost.

SUMMARY OF THE INVENTION

It has been discovered that polyethylene glycol and other material, such as polymeric polyols, or dextran or polyvinyl chloride, can attach to a solid phase base and also have the capability of absorbing immune complexes which may be present in a specimen of human serum or the like and be effective to produce reliable immunoassay analyses. After the attachment of the polymer having such properties to the solid phase base, such as a micro-titer plate, test tube or the like, the steps used in the assay method of this invention may be similar to the corresponding steps of the ELISA assay. However, the solid phase base must be one to which the polymer will attach and a plastic has been found to be the preferred material for the base, particularly polystyrene and polyvinyl chloride or any other material which will function in such a manner with the materials disclosed herein.

After the specimen has reacted with the polymer, a radioactive material may be utilized, such as an anti-human IgG-$I^{125}$ which may be reacted with the immune complexes adsorbed by the polymer. Excess reactants may then be removed and the amount of radioactive material reacting with the adsorbed immune complexes measured, as by a scintillation counter, or the like, to achieve the assay.

The article of this invention, useful in an immunoassay analysis, is a solid phase base having means for receiving a layer of the polymer and also a specimen to be tested, such as a series of wells in a planar surface of a titer plate or the cavity of a test tube, which is preferably formed of plastic and not of glass, with such means having a coating or layer of a liquid phase, non-proteinaceous, non-ionic polymer having the capability of absorbing immune complexes. The method of producing such an article is the same as the first few steps of the assay method described previously. Also, the article is preferably protected by a layer or film which covers the polymer and specimen receiving means to delay evaporation of the layer of liquid phase material.

THE DRAWINGS

DESCRIPTION OF THE PREFERRED EMBODIMENT

Figure 1:
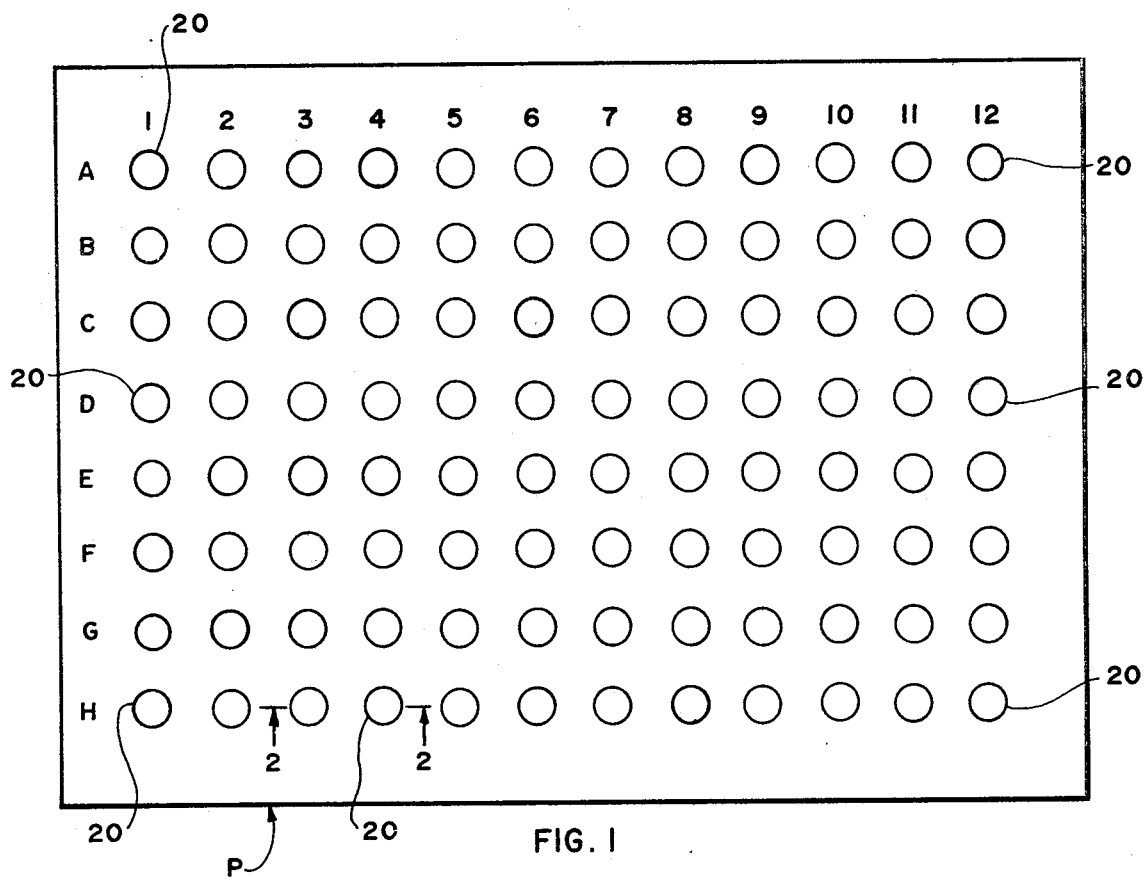
FIG. 1 is a top plan view of a plastic micro-titer plate which is adapted to form the article of this invention and is particularly useful in the immuno-assay thereof.
Figure 3:
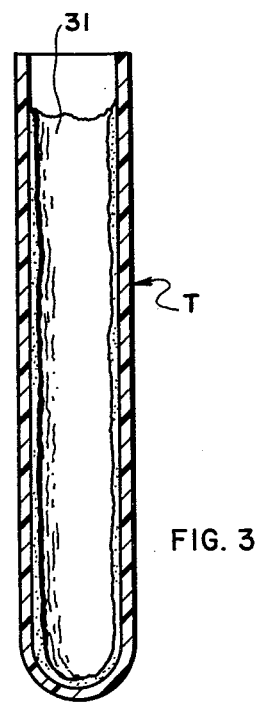
FIG. 3 is a longitudinal section, on an enlarged scale, of a test tube comprising another article useful in the immunoassay of this invention.

A solid phase base adapted to receive a test specimen, such as a microtiter plate P of FIG. 1, or test tube T of FIG. 3, is treated in accordance with this invention for use in the detection of immune complexes, e.g. antigen antibodies, such as are present in a human serum sample of a patient suffering from rheumatoid arthritis, tumor, hepatitis, viral infection or the like. Each of the plate P and test tube T are formed preferably of a suitable plastic, such as polystyrene or polyvinyl chloride. Plate P is provided with a series of wells 20, of a capacity as small as on the order of 0.2 cc, while the capacity of test tube T may be on the order of about 5.0 cc. For testing, a substantial number of specimens of human serum, such as blood plasma or cerebral spinal fluid, together with a desired adequate number of controls, are placed in the wells 20 of the plate P. The wells of plate P may be provided in any suitable manner but are here divided into both horizontal and vertical rows, with suitable indicia systems to indicate each specific well. In the system shown in FIG. 1, the wells of the vertical rows may be numbers, as from 1 through 12, while the wells of the horizontal rows may be identified by letters, as from A through H, to provide a more accurate correlation of the results with the samples being tested. As will be evident, there are 96 wells shown in FIG. 1, although the specific number may be varied as desired.

In accordance with this invention, a solution of a non-proteinaceous, non-ionic organic polymer which is also capable of absorbing immune complex, as well as wetting the plastic of plate P and test tube T, is utilized, with the preferred non-ionic polymer being polyethylene glycol, PEG, i.e. p-isooctyl phenyl ether. The PEG should range in molecular weight from about 2,000 to about 20,000 with a molecular weight of 6,000–8,000 preferred. A solution of PEG, having a PEG concentration of about 5% to about 20%, with 9% being preferred, is poured or dipped onto plate P, or deposited in each well 20. After 12 to 24 hours, any excess PEG is shaken off the plate, leaving a layer 21 of FIG. 2, comprising PEG adhering to each well of the plate. A similar operation may be utilized in coating the inside of test tube T of FIG. 2 with a PEG layer 31, as by pouring the PEG solution into the test tube, letting it stand typically for 12 to 24 hours, then shaking out the excess solution.

Figure 4:
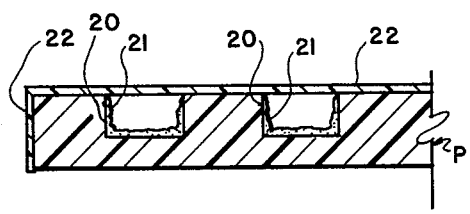
FIG. 4 is a cross section similar to FIG. 2 but taken at a position so as to include an edge of the titer plate of FIG. 1 and showing also a protective layer which prevents or delays the evaporation of a liquid polymer which is adhered to the wells of the titer plate.

It is also contemplated that polyethylene glycol polymers or adducts having a molecular weight of about 2000 to about 20,000 should be able to be used successfully in the present invention. Tests would indicated that polymeric materials having the proper wetting and reactivity characteristics should be suitable for use according to the present invention. The non-ionic polymer so deposited on the plate should be protected from the air, as by a protective means such as the layer or film 22 of FIG. 4, since exposure to the air, as indicated in Example 3, for too long a time may result in the solvent evaporating, with the PEG becoming a powder and washing away when the serum is added, as described hereinafter.

Most preferably it is desirable to wash the PEG solution from the wells of plate P with a buffer solution before reacting the PEG with the immune containing serum. Typically a carbonate-bicarbonate buffer solution may be utilized, at a pH of about 7.6, such as indicated by the following Table 1:

TABLE 1

| | |
|---|---|
| $Na_2CO_3$ | 1.5 g. |
| $NaHCO_3$ | 2.9 g. |
| $H_2O$ | 1 liter |

Other buffer systems may be utilized, such as the phosphate buffer solution of Table 2, having a pH of about 7.4:

TABLE 2

| | |
|---|---|
| NaCl | 8 g. |
| $KH_2PO_4$ | 0.2 g |
| $Na_2HPO_3 12H_2O$ | 2.9 g. |
| KCl | 0.2 g. |
| $H_2O$ | 1 liter |

In each instance, an appropriate amount of PEG can also be added to the buffer solution. Also, if a non-buffered, aqueous solution of PEG has been added, a buffer solution may be added with the serum. It has been found that the titer plate, test tube or the like must be formed of plastic, since otherwise the non-ionic polymer useful in this invention may not produce adequate adherence to a titer plate or test tube of glass.

The application of the serum and the remainder of the assay may be conducted similarly to the standard ELISA assay described herein, in which a protein is utilized as the antigen, such as described in the 1979 book entitled *The Enzyme Linked Immunosorbent Assay* (*ELSIA*) by Bidwell and Bartlett. FIG. 6 of this book is a chart of the indirect method for assay of antibody, which is described as being carried out as follows:

1. The relevant antigen is attached to the solid phase, then washed.
2. The diluted test serum is added, and incubated, followed by washing.
3. An enzyme-labeled anti-species-globulin is added and allowed to react, then washing is repeated. Unlabeled anti-species-globulin followed by labeled antigen to this second antibody can also be used.
4. The enzyme substrate is added. Degradation of substrate results in a colour change. The amount and rate of colour change is related to the amount of antibody in the test serum in step 2.

After the titer plate P has been treated to provide the PEG layer 21, an appropriate amount of the human serum to be tested or control serum or control solution, is placed in a well 20 of the titer plate, for instance, for absorption by the PEG layer 21. For instance, 50 µl. of serum may be added to the appropriate well 20 by a calibrated pipetts, then left to stand, as at 37° C. for one hour or a longer time, as up to two hours, at a lesser temperature, such as from 37° C. down to 4° C.

Following the above, the layer 21, in which the immune complexes have been absorbed, is washed, preferably three times, with a lightly saponified phosphate solution, such as the phosphate buffer solution of Table 2, to which has been added 0.5 ml. of "Tween 20", a standard detergent available from Sigma Chemical of St. Louis, Mo. Other equivalent detergents may, of course, be utilized. The preferable washing is for three times. Thus, one, two, three and four washings of different tests have indicated that three washings are desirable, but that the fourth appeared to produce no detectable improvement in the accuracy of the test.

Following washing, the comparative amount of immune complex bound to the PEG may be determined by the conventional radioactive method, such as involving the use of anti IgG-I$^{125}$, washing off excess of the latter and then measuring the amount of immune complex reactive by the use of a scintillation counter to determine the presence and amount of radioactive material. However, it has been discovered that the use of radioactive material may be dispensed with and the results procured more quickly, in comparison with previous tests involving the use of protein, by performing an enzyme linked immunosorbent assay, i.e. ELISA test, described at many places in the literature and specifically hereinbefore. As indicated, previous tests have used protein only for the determination of immune complexes and not a non-proteinaceous, non-ionic organic polymer. Thus, the present invention includes the addition of an anti-human IgG coupled with an enzyme, a conventional product available from Sigma Chemical. After the enzyme has been added, the layer is permitted to stand, as at 37° C. for up to two hours, after which it is washed about four times with the phosphate buffer detergent solution of Table 2 or this phosphate buffer solution to which 9% of PEG has been added.

When the enzyme selected is a phosphatase, the substrate should preferably be p-nitro phenyl phosphate, and the concentration on the order of 1 mg. per ml., while 200 μl of the substrate solution of Table 3, is then added to each well of the plate. When the enzyme selected is a peroxidase, the substrate can be phenylene diamine phosphate with a small amount of $H_2O_2$; when the enzyme selected is B-galactosidase, the substrate can be a galactoside; for other types of antibody coupled enzymes, an appropriate substrate should, of course, be utilized. The selection of a suitable substrate is within the purview of one skilled in the art of immuno-assay works.

Following the above steps, the next reaction is with a color reagent, such as through the addition of a substrate specific for the enzyme which has been to the solution of Table 3 at pH 9.8:

TABLE 3

| Diethanolamine | 10 g. |
|---|---|
| $MgCl_2.6H_2O$ | 100 mg. |
| $H_2O$ | 800 ml. |

The reaction with the color reagent, which takes place at room temperature, will produce a color change, if any is to be produced, within about 30 minutes. The reaction will produce a color change dependent upon the amount of immune complex bound to the plate. A color ranging from the absence of color to a very pale yellow represents less than a significant amount of immune complex. An intense yellow color can represent a fairly large amount of immune complex. A spectrophotomer, of the type usually utilized in ascertaining the results of an ELISA test, is generally more reliable than the human eye. Such a spectrophotomer, it is suggested should be read at an absorbence of 405 nanometers for a phosphate washed substrate. Typically, such a substrate could produce a reading of less than 0.060 O.D. units when observing a normal serum. Conversely, a heat aggregated human gamma gobulin, heated to 63° C. for 30 minutes, has produced a reading of more than 0.060 O.D.

Commercially available polyethylene glycol or PEG (as that term is understood) can conceivably be more effective than a non-ionic organic polymer which is potentially reactable or physically compatible with both the plate P or test tube T and the immune complexes, such as dextran or polyvinyl chloride, since the latter is less effective and less selective than polyethylene glycol. It is theorized, though not definitively determined, that the interaction with immune complexes may be due to steric exclusion of the complexes from the domain of the PEG, based on immuno-precipitation characteristics of the PEG as suggested by Rampling, M. W. *Biochemical Journal* (1974). The present discovery is unexpected because the polymer is immobile on a solid phase base, rather than mobile in the solution, as reported, so that the theory of steric hindrance does not appear to explain the results observed herein. In any event, the use of PEG or any other polymer of this invention has not been suggested or tried for absorption of an immune complex onto a solid phase base as prepared herein.

In addition to reacting the polymer with the solid phase base, then adding the serum, it also appears possible to mix the polymer with the serum and simultaneously deposit the polymer on the solid phase base for reaction with both the base and the serum. The addition of a buffer to the solution, as of Table 1 or Table 2, also appears desirable, with the remainder of the steps, including washing and testing, proceeding as before.

Further, the formation and measurement of immune complexes formed in vitro may be utilized, according to the present invention, to determine the probable presence or absence of a predetermined suspected condition of the patient. A sample of the same serum which is also tested without such reaction, can be reacted in a test tube the suspected antigen, which may result in the formation of immune complexes. For instance, in order to test for hepatitis antibody, a sample of the serum may be reacted in a test tube with hepatitis virus, such as for one hour at 37° C., accompanied by gentle shaking. The resultant will be used as one sample in a test of this invention, with another sample being serum which has not been reacted with the virus. Then, if the sample which has been reacted with hepatitis virus produces a high reading, with respect to the presence of immune complexes, while the normal serum produces a much lower reading but shows the presence of immune complexes, this result will be an indication that the antibodies which are specific for hepatitis are produced as a result of the presence of immune complexes. To test for the presence of a condition due to any other particular disease, a bacteria productive of that disease can be reacted with a sample of the serum and a comparison of the results of the test of such reacted serum, with the test of the normal serum, is an indication of whether the presence of immune complexes is due to such bacteria. For a test to indicate the presence or absence of rheumatoid arthritis, a sample of the serum from a patient can be reacted with human immunoglobulin G (IgG), which will act as an antigen to form immune complexes. When the sample so reacted is tested along with a normal sample of the serum, a comparatively high reading for the sample reacted with the IgG and a considerably lower reading for the normal (unreacted) sample will be an indication that the presence of the immune complexes has been produced by antibody to IgG. In a similar manner, DNA may be added to a serum sample in order to determine the presence or absence of systemic lupus erythamatosus, i.e. SLE. Similar indication with respect to other suspected conditions can be obtained by adding an appropriate virus, bacteria, or other antigens to one serum sample and simultaneously testing a normal (unreacted) serum sample.

The efficacy of the solid phase base reacted with the polymer and the testing of serum for immune complexes has been demonstrated by the following examples.

EXAMPLE 1

A titer plate corresponding to plate P of FIG. 1 was used. A carbonate-bicarbonate buffer solution of Table 1, containing 9% PEG having a molecular weight of about 6000, was added to the wells 20, the plate allowed to stand for 12 hours at 37° C., then the excess solution shaken off to provide the layers 21 of FIG. 2 in the wells 20. Then, duplicate samples of human serum obtained from various patients of a hospital were placed in 72 of the 96 wells of the plate. In addition, negative controls of serum from babies who presumably had no immune complexes were placed in 21 of the wells, while 4 positive controls, consisting of serum from patients who had been clinically diagnosed as having rheumatoid arthritis, were placed in four of the wells. Also, a control to test the function of the substrate, consisting of anti-human IgG antigen labeled with a phosphatase enzyme, was placed in one well. After addition of the serum and sample, the plate was left standing for one hour at 37° C. to permit the immune complexes, if any, of the serum specimens to react with the PEG layers. Then, the wells were each washed three times with the phosphate buffer solution of Table 2 to which had been added 0.5 ml. of "Tween 20" detergent.

Following washing, an anti-human IgG immunoglobulin labeled with a phosphatase enzyme was added to the wells and allowed to incubate for two (2) hours at 37° C. After incubation, the excess antisera was removed and the plate was washed three (3) times with the phosphate buffer solution of Table 2 containing "Tween 20" detergent.

Following washing, a diethanolamine solution of Table 3 to which p-nitro phenyl phosphate had been added, as described previously, was added to each well and the reaction, if any, permitted to take place. After 30 minutes at 37° C., the color of the reacted layers in the respective wells was measured with a spectrophotomer, read at an absorbence of 405 nanometers. As expected, the well containing the substrate function test, i.e. enzyme labeled anti-human IgG antiserum had a reading of 2.0, while 20 of the 21 assumed normal samples or negative controls read from 0.001 to 0.07 and two read 0.000, while one assumed normal sample read 0.793, which was suggestive of an immune complex type disorder. The remaining test readings ranged from 0.02 to 0.575, with the differences in the readings for duplicate specimens approximating the differences for duplicate specimens, within the inventor's experience relating to the use of a protein coating on a solid phase, plastic base and an ELISA assay or a Raji cell radioimmuno assay. It was thus concluded that the above test equaled the reliability of the radioimmuno assay and the ELISA assay, each using protein as the layer reacting with plastic.

EXAMPLE 2

Figure 2:
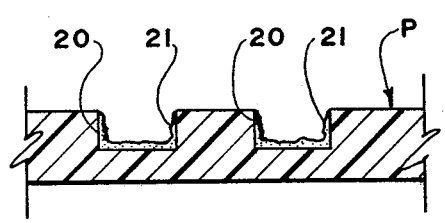
FIG. 2 is a fragmentary cross section, taken along line 2—2 of FIG. 1 on an enlarged scale, showing the micro-titer plate prepared for use.

A titer plate corresponding to plate P of FIG. 1, was treated in the same manner as in Example 1, to produce the PEG layers 21 of FIG. 2. Then, 32 human serum specimens obtained from a hospital were placed in 64 wells of the titer plate, i.e. with a duplicate of each specimen. Nine negative controls, two positive controls and one substrate control were also utilized. The same procedures as in Example 1 were followed, with testing of the color produced in the same manner.

All of the negative controls produced a reading of 0.00, while the two positive controls produced readings of 0.78 and 0.62, respectively, and the substrate control produced an intense yellow color and a reading of 0.8881. The highest reading, other than the controls, was 0.739 for a patient who was actually quite ill. Thirty-five of the samples produced readings of less than 0.060, the number being accounted for by the fact that duplicate specimens produced one reading of less than 0.060 and the other slightly higher than 0.060. Of the remaining readings, eight were between 0.060 and 0.100, seven were between 0.101 and 0.200, three were between 0.201 and 0.300, two were between 0.301 and 0.400, while two duplicate readings were above 0.401, i.e. 0.519 and 0.737, as noted above. Again, the variance in the readings of duplicate specimens approximated the experience of the inventor with respect to readings produced by duplicate specimens when using a protein on a solid phase, plastic base and an ELISA assay or a Raji cell radioimmuno assay.

The following example shows the necessity for maintaining the liquid or wet condition of the polymer.

EXAMPLE 3

A titer plate corresponding to plate P of FIG. 1 was treated in the same manner as in Example 1, to produce the PEG layers 21 of FIG. 2. The plate was allowed to stand unprotected for four days at 37° C. When the plate was then desired to be used for testing samples of heat aggregated human gamma globulin, it was found that the buffer solution had evaporated, leaving a layer of powder on the plate, apparently PEG. Much of this powder washed away when a test solution was placed in a well, showing that any serum added to the wells would wash away the powder and that the plate was not usable for any further steps in the test.

The following examples, carried out prior to Examples 1 and 2, show the comparative results of tests in accordance with this invention, using heat aggregated human gamma globulin, utilized as positive controls in Examples 1 and 2.

EXAMPLE 4

A tilter plate corresponding to plate P of FIG. 1 was treated in the same manner as in Example 1, to produce the PEG layers of FIG. 2, while a human serum was heated at 63° C. for 30 minutes, to provide heat aggregated human gamma globulin. The plate was washed with the solution of Table 2 to which 0.5 ml. of "Tween 20" had been added. Two wells 20 of FIG. 2 were filled with the heat aggregated gamma globulin, diluted with water in a 1:4 ratio, while a 1:4 solution of the wash solution was added to two other wells. The plate was shaken occasionally but maintained at 37° C., then washed twice with the solution as previously used. To each of the four wells was added a 1:200 dilution of anti-human IgG coupled with phosphatase enzyme, then permitted to incubate for one hour. The plate was then washed twice with the same wash solution and a p-nitro phenyl phosphate substrate in the amount of 1 mg. per ml. in the substrate solution of Table 3 was added. After 40 minutes, the wells were examined by eye and it was found that the wells containing the wash solution were both clear and without color, whereas the wells initially containing the human gamma globulin were clear but an intense yellow in color.

EXAMPLE 5

A titer plate corresponding to plate P of FIG. 1 was treated in the same manner as in Example 1 to produce PEG layers 21 of FIG. 2, while a human serum was heated as in Example 4 to produce human gamma globulin. Various specimens were made at increasing dilutions, as in Table 4 below, and the test proceeded as in Example 4, except that the color of the substrate was measured by a spectrophotometer as in Examples 1 and 2. The readings obtained, at an absorbance of 405 nanometers, are set forth below in Table 4.

TABLE 4

| Dilution | Reading of photospectrometer |
|---|---|
| 1:8 | 0.360 |
| 1:16 | 0.299 |
| 1:32 | 0.192 |
| 1:64 | 0.101 |
| 1:128 | 0.048 |
| 1:256 | 0.006 |
| 1:512 | 0.000 |
| 1:1024 | 0.000 |

When the above readings were plotted on a graph, with the decimal readings plotted as ordinates and the dilution factors plotted as abscissa on a geometric basis, i.e. with the successive dilutions indicated above spaced apart equally, a straight line was formed by the points for the 1:8 through the 1:128 dilutions. The reading for the 1:256 dilution was above the slope of the straight line, if extended, while the 1:512 and 1:1024 readings were on the abscissa axis. Since such a straight line is typical of reliable ELISA tests, it was considered that the reliability of the present test had been demonstrated.

EXAMPLE 6

The wells of a titer plate, corresponding to plate P, were coated with a 9% solution of PEG having a molecular weight of 6000, and then washed, as in Example 5. One series of samples was prepared from heat aggregated gamma globulin, produced as in Example 4, and aqueous solutions of various dilution were prepared therefrom with the dilution of Table 4 above. To test the sensitivity of the procedure, human serum was repeatedly frozen and thawed, to produce aggregated gamma globulin and a second series of samples were similarly diluted in aqueous solution, as in Table 5. Then ®µl. of each sample were added to a well of the plate and 90 minutes at room temperature allowed for incubation. The plate was then washed two times with the solution of Table 2 to which 0.5 ml. of "Tween 20" had been added. Then, 200 µl of antihuman IgG coupled with phosphatase enzyme and diluted 1:500 was added to each well and permitted to incubate for 90 minutes, then washed two times with the above washing solution. A substrate was added to each well, i.e. 200 µl of p-nitro phenyl phosphate in the substrate solution of Table 3 permitted to react for 40 minutes and then quenched with a 3 N NaOH solution.

The following Table 5 shows the results of observation by the eye which, although not as accurate as readings by a spectrophotometer, were sufficient to show the sensitivity of the test.

TABLE 5

| Dilution Proportion | Heat Aggregation Sample | Freeze and Thaw Specimens |
|---|---|---|
| 1:8 | ++ | ++ |
| 1:16 | ++ | ++ |
| 1:64 | ++ | ++ |
| 1:128 | ++ | +/− |
| 1:512 | +/− | − |
| 1:1024 | +/− | − |
| 1:2048 | − | − |

Where:
++ indicates strong color
+/− weak color
− clear solution, with no yellow The following example was an experiment to compare polyethylene glycol having a molecular weight of 20,000 with that having a molecular weight of 6,000:

EXAMPLE 7

A 10% solution of PEG having a molecular weight of 20,000 was used to coat one plate corresponding to plate P of FIG. 1 and a 10% solution of PEG of 6,000 molecular weight was used to coat an identical plate. Each plate was washed with the phosphate solution of Table 2 to which "Tween 20" had been added, as before. Normal human serum was heated as in Example 4, but excess serum was centrifuged off and the remainder made into duplicate samples having the dilutions set forth in Table 6 below. Samples of the various dilutions were added to each plate and left at room temperature for 3½ hours, accompanied by shaking and followed by washing two times with the sapoinified phosphate solution. A 1:200 solution of antihuman IgG coupled with an enzyme was added to each well and the plates shaken in a micro-mixer for between 10 and 15 minutes, then allowed to incubate at 37° C. for 30 minutes and at room temperature for 1½ hours. Each plate was then washed with the lightly saponified phosphate solution and 200 µl of p-nitro phenyl phosphate substrate, as in Example 4, was added to each well. After 20 minutes, the wells containing samples were examined visually, with the results indicated in Table 6.

TABLE 6

| Dilution Proportion | Layer of PEG 6000 | Layer of PEG 20,000 |
|---|---|---|
| 1:8 | ++ | − |
| 1:16 | ++ | +/− |
| 1:32 | ++ | +/− |
| 1:64 | ++ | +/− |
| 1:128 | ++ | + |
| 1:256 | +++ | +/− |
| 1:512 | ++ | +/− |
| 1:1024 | +++ | − |
| 1:2048 | − | − |
| 1:4096 | − | − |

Where:
+++ indicated greatest intensity
++ indicated strong color
+/− indicated weak color
− indicated clear solution, no color From the above test, it was concluded that the PEG 6000 appeared to react with the immune complexes more effectively.

It will be understood that other embodiments of this invention, other than those described or indicated, may be utilized and that various changes may be made without departing from the spirit and scope of this invention.

What is claimed is:

1. In a method of performing an immunoassay of a fluid specimen to determine immune complexes therein, the steps comprising:

treating a solid phase, plastic base having means for receiving the fluid specimen to be assayed, to produce a layer of a non-proteinaceous non-ionic polymer on said means, said polymer adhering to said plastic base and having the capability of absorbing immune complexes which may be present in such specimen;

placing the fluid specimen to be assayed on said receiving means;

permitting said polymer layer to absorb immune complexes present in said specimen; and treating said layer in a manner to produce an indication of the amount of immune complexes in said layer.

2. In a method as defined in claim 1, wherein:
said polymer is selected from the group consisting of polyethylene glycol, dextran and polyvinyl chloride.

3. In a method as defined in claim 1, wherein:
said non-ionic polymer is polyethylene glycol having a molecular weight from about 2000 to about 20,000.

4. In a method as defined in claim 1, wherein:
said polymer is a polymeric polyol.

5. In a method as defined in claim 1, wherein:
said indication treatment produces a change in color, generally proportional to the amount of immune complexes absorbed by said layer; and
measuring the color so produced by visual or spectrophotometric means.

6. In a method as defined in claim 5, which includes:
washing said base a plurality of times with a buffer solution following production of said polymer layer thereon;
washing said plate, after absorption of immune complexes of said specimen by said polymer layer, a plurality of times with a buffer solution;
adding an anti-human IgG coupled with an enzyme to said layer and permitting said layer to stand for a predetermined time;
washing said layer a plurality of times with a buffer solution after said layer is permitted to stand for said predetermined time;
adding a substrate reactive with said anti-human IgG coupled with an enzyme to produce a color change proportional to the amount of said anti-human IgG coupled with an enzyme which has reacted with immune complexes present in said layer; and
measuring the color change in said layer by means of a spectrophotometer.

7. In a method as defined in claim 1, wherein:
said indication treatment involves a radioactive agent which produces a radiation intensity generally proportional to the amount of immune complex absorbed by said layer; and
measuring the amount of radiation present.

8. In a method as defined in claim 1, which includes:
treating a second fluid specimen, essentially identical to said first specimen, with a virus or bacteria of a suspected condition; and
performing an immunoassay on said second specimen simultaneously with said first specimen.

9. In a method of performing an immunoassay of a fluid specimen to detect immune complexes therein, the steps comprising:

placing the fluid specimen on a receiving means of a solid phase, plastic base having at least one receiving means, with said receiving means having a layer of a non-proteinaceous, non-ionic polymer adhering thereto and having the capability of absorbing immune complexes from such specimens;

placing the fluid specimen to be assayed on said receiving means;

permitting said polymer layer to absorb such immune complexes; and treating said layer in a manner to provide an indication of the amount of immune complexes in said layer.

10. In a method as defined in claim 9, wherein:
said polymer is selected from the group consisting of polyethylene glycol, dextran and polyvinyl chloride.

11. In a method as defined in clim 9, wherein:
said non-ionic polymer is polyethylene glycol having a molecular weight from about 2000 to about 20,000.

12. In a method as defined in claim 9, wherein:
said polymer is a polymeric polyol.

13. In a method as defined in claim 9, wherein:
said indication treatment produces a change in color, generally proportional to the amount of immune complexes absorbed by said layer; and
measuring the color so produced.

14. In a method as defined in claim 13, which includes;
washing said base a plurality of times with a buffer solution following production of said polymer layer thereon;
washing said plate, after absorption of immune complexes of said specimen by said polymer layer, a plurality of times with a buffer solution;
adding an anti-human IgG coupled with an enzyme to said layer and permitting said layer to stand for a predetermined time;
washing said layer a plurality of times with a buffer solution after said layer is permitted to stand for said predetermined time;
adding a substrate reactive with said anti-human IgG coupled with an enzyme to produce a color change proportional to the amount of said anti-human IgG coupled with an enzyme which has reacted with immune complexes present in said layer; and
measuring the color change in said layer by means of a spectrophotometer.

15. In a method as defined in claim 9, wherein:
said indication treatment involves a radioactive agent which produces a radiation intensity generally proportional to the amount of immune complex absorbed by said layer; and
measuring the amount of radiation present.

16. In a method as defined in claim 9, which includes:
treating a second fluid specimen, essentially identical to said first specimen, with a virus or bacteria of a suspected condition; and
performing an immunoassay on said second specimen simultaneously with said first specimen.

* * * * *